United States Patent [19]
Tuloup et al.

[11] Patent Number: 5,972,313
[45] Date of Patent: Oct. 26, 1999

[54] ACTIVE/STABLE ARTIFICIAL TANNING COMPOSITIONS COMPRISING DHA DERIVATIVES

[75] Inventors: Rémy Tuloup, Paris; Christian Blaise, Saint Mande; Michel Philippe, Wissous; Daniel Sera, L'Hay les Roses; Armelle De Salvert, Paris, all of France

[73] Assignee: Societe L'Oreal S.A., Paris, France

[21] Appl. No.: 08/819,084

[22] Filed: Mar. 18, 1997

[30] Foreign Application Priority Data

Mar. 18, 1996 [FR] France ................................ 96 03344

[51] Int. Cl.$^6$ ........................................ A61K 7/42
[52] U.S. Cl. ........................ 424/59; 424/401; 424/450; 514/844; 514/846; 514/937; 514/938; 514/944; 560/60; 560/179; 560/188
[58] Field of Search .......................... 424/401, 59, 450; 560/60, 179, 188; 514/844, 846, 937, 938, 944

[56] References Cited

FOREIGN PATENT DOCUMENTS 0671159 9/1995 European Pat. Off. .
94/12146 6/1994 WIPO .

OTHER PUBLICATIONS

Journal of Pharmaceutical Sciences, vol. 60, No. 7, Jul. 1971, Washington US, pp. 1083–1085, Garson et al, "Unsymmetrical Carbonates as Potential Long–Lasting Insect Repellants".

*Primary Examiner*—Jyothsna Venkat
*Attorney, Agent, or Firm*—Burns, Doane, Swecker & Mathis, L.L.P.

[57] ABSTRACT

Stable, topically applicable cosmetic/dermatological compositions well suited for artificially tanning or browning human skin and appropriately packaged, comprise at least one dihydroxyacetone (DHA) derivative convertible into DHA and, advantageously, at least one active species for effecting such conversion.

33 Claims, No Drawings

ACTIVE/STABLE ARTIFICIAL TANNING COMPOSITIONS COMPRISING DHA DERIVATIVES

BACKGROUND OF THE INVENTION

1. Technical Field of the Invention

The present invention relates to novel cosmetic or dermatological compositions comprising at least one dihydroxyacetone (hereinafter sometimes "DHA") derivative. More especially, this invention relates to novel artificial or self-tanning compositions having improved activity and stability.

The present invention also relates to novel dihydroxyacetone derivatives, per se.

2. Description of the Prior Art

It is known to this art that dihydroxyacetone, or DHA, is a particularly advantageous compound which is commonly employed in the cosmetics field as an agent for the artificial tanning of the skin. When topically applied to human skin, in particular to the face, it elicits a tanning or browning effect, the appearance of which is similar to that which may result from prolonged exposure to the sun (natural tan) or under a UV lamp. Such a use, moreover, presents the advantage of totally avoiding the risks of skin reaction which are generally associated with the aforesaid prolonged exposures (erythema, burning, loss of elasticity, appearance of wrinkles, premature aging of the skin, and the like).

However, the use of DHA also presents many drawbacks. Essentially, these appear during storage of compositions containing DHA and are quite incompatible with the expectation of the consumer. Thus, DHA has an annoying tendency, which is more or less pronounced depending on the nature of the medium in which it is formulated, to degrade over time. This degradation generally is reflected over time by an undesirable yellowing of the compositions containing same. It also occurs that, over time, such compositions develop a nauseating odor. Lastly, the pH of compositions containing DHA decreases over time, in the long run rendering same incompatible for use in topical applications (pH of the skin in the region of 5.5).

The result of the above phenomena, encountered during the period of storage of compositions containing DHA, is that the activity of the DHA, and in particular its ability to color the skin, is greatly decreased when these compositions are applied to the skin. Thus, the intensity of the coloration obtained on the skin and/or the speed with which this coloration develops may appear as still insufficient. It is also known that the content of DHA on the skin is not perfect.

In order to increase the speed of appearance of the coloration due to DHA or the resistance of the latter over time, it has been attempted to combine DHA with other substances. Thus, EP-A-547,864 describes providing DHA in the presence of an amino acid and a silicone, the DHA and the amino acid being stored before application to the skin in separate compartments. Too, WO-A-94/04,130 describes a device for providing DHA at the same time as a primary amine, these two compounds also being stored in separate compartments.

However, these devices do not entirely solve the problems of yellowing, of odor and of instability due to storage of the DHA.

SUMMARY OF THE INVENTION

It has now unexpectedly been found that particularly stable artificial/self-tanning compositions having surprising qualities in terms of intensity and staying power on the skin are provided by formulating at least one specific DHA precursor into cosmetic or dermatological compositions.

By the term "DHA precursor" is intended a compound other than DHA, but which is converted into the latter by reaction with one or more specific compounds.

Briefly, the present invention features cosmetic or dermatological compositions comprising, in a cosmetically or dermatologically acceptable vehicle, diluent or carrier, at least one dihydroxyacetone derivative having the following formula (I):

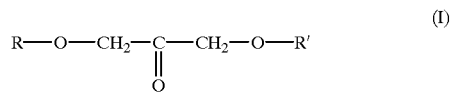

in which R and R', which may be identical or different, are each a hydrogen atom or an alkyloxycarbonyl or arylalkyloxycarbonyl radical which is optionally hydroxylated or which contains a cyclic carbonate or an oxide ether bridge, such radical having from 2 to 25 carbon atoms, being linear or branched or cyclic, and saturated or unsaturated, with the proviso that R and R' cannot simultaneously each be a hydrogen atom.

DETAILED DESCRIPTION OF BEST MODE AND SPECIFIC/PREFERRED EMBODIMENTS OF THE INVENTION

More particularly according to the present invention, the subject novel cosmetic compositions present the advantage of being stable over time and of not degrading when they are stored. The reason for this is that they contain no DHA, per se.

Another advantage of the subject compositions is that, once they are topically applied to the skin, they have very good staying power. The reason for this is that such compositions provide a DHA precursor in the form of a DHA derivative. By reacting with one or more compounds of the skin which are capable of cleaving its (or their) carbonic ester bond(s), this precursor produces DHA when the composition is applied to the skin. The activity of the DHA on the skin in terms of intensity and staying power is thus particularly effective.

Although compounds capable of hydrolyzing the DHA derivative(s) are present on the skin in an amount which is sufficient to attain a very satisfactory result, the efficacy of the compositions according to the invention may be further enhanced by providing compounds of this type at the same time as the DHA derivatives(s).

Thus, the present invention also features cosmetic/dermatological compositions comprising, in a cosmetically or dermatologically acceptable vehicle, diluent or carrier:

(i) at least one dihydroxyacetone derivative having the general formula (I):

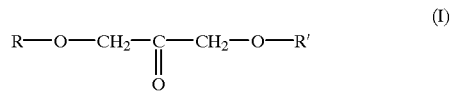

in which R and R', which may be identical or different, are each a hydrogen atom or an alkyloxycarbonyl or arylalkyloxycarbonyl radical which is optionally hydroxylated or which contains a cyclic carbonate or an oxide ether bridge, such radical having from 2 to 25 carbon atoms, being linear or branched or cyclic, and saturated or unsaturated, with the proviso that R and R' cannot simultaneously each be a hydrogen atom, and (ii) at least one compound capable of cleaving at least one carbonic ester bond.

Such a composition is very stable over time and has particularly good staying power on the skin.

In a preferred embodiment of the invention, the radicals R and R' have from 2 to 18 carbon atoms.

Preferably also, R and R' are each an ethyloxycarbonyl, benzyloxycarbonyl, octyloxycarbonyl, oleyloxycarbonyl, isopropyloxycarbonyl, decyloxycarbonyl or carbonyldioxy-2,3-propyloxycarbonyl radical and, even more preferably, the radicals R and R' are identical.

Advantageously, the derivative is selected from the group consisting of:

1,3-diethylcarbonato-2-propanone,
1,3-diisopropylcarbonato-2-propanone,
1,3-didecylcarbonato-2-propanone, and
1,3-di(carbonyldioxy-2,3-propylcarbonato)-2-propanone.

In another preferred embodiment of the invention, the DHA derivative may be present in the compositions of the invention at a concentration ranging from 0.1% to 30% by weight relative to the total weight of the composition, and preferably at a concentration ranging from 0.5% to 15% by weight relative to the total weight of the composition.

According to the invention, and in a specific embodiment thereof, the compound capable of cleaving at least one carbonic ester bond may be any nucleophilic compound which is acceptable in the cosmetic and dermatological fields. Thus, exemplary thereof are the alcohols, thiols, amines or anions.

Among the amines, a hydroxylated amine such as, for example, 3-amino-1,2-propanediol, 2-amino-2-methyl-1,3-propanediol, 2-amino-2-methylpropanol or 2-amino-2-hydroxymethyl-1,3-propanediol, glucamine, n-methylglucamine or an amino acid such as, for example, lysine, arginine or histidine, is preferably selected.

Among the anions, a carboxylate anion such as, for example, salts of fatty acids, of amino acids or of lipoamino acids, is preferably selected.

The compound capable of cleaving at least one carbonic ester bond may be employed at a concentration ranging from 0.1% to 30% by weight relative to the total weight of the composition and preferably ranging from 0.5% to 15% by weight relative to the total weight of the composition.

It is preferable, in the common usage of such compositions, to ensure that the hydrolysis of the DHA derivative occurs only when the composition(s) is (or are) actually applied. It is therefore advantageous to provide packaging such that the DHA derivative and the compound capable of cleaving at least one carbonic ester bond are packaged such as not to be in direct contact with each other.

Accordingly, the present invention also features packaging provided with at least two compartments, one of the compartments containing a composition (A) comprising, in a cosmetically acceptable vehicle, diluent or carrier, at least one compound of formula (1) as defined above and the other compartment containing a composition (B) comprising, in a cosmetically acceptable vehicle, diluent or carrier, a compound capable of cleaving at least one carbonic ester bond as defined above, said compartments being physically separate such that said compositions (A) and (B) are not in contact with each other.

Advantageously, the two compartments are integral and arranged to constitute a single body, each of which respectively permitting the expulsion of composition (A) and composition (B) and admixture thereof, said expulsions being either simultaneous or separate. The mixing takes place during application.

Advantageously, the single body is in the form of a flexible tube.

Another form of packaging containing two separate but integral compartments may be such that the derivative is packaged in a different form from the compound capable of cleaving a carbonic ester bond: for example, the composition (A) may be in the form of microcapsules or spherules encapsulating the compound of formula (1) and the composition (B) may be in the form of a cream, a gel or any other classical formulation wherein the compound capable of cleaving at least one carbonic ester bond is not encapsulated, the microcapsules or spherules constituting the composition (A) being immersed in the composition (B).

In another embodiment of the invention, the compositions described above, namely, the DHA derivative and the compound for hydrolyzing the DHA, can be encapsulated separately of each other. Such preparations are formulated by the usual encapsulation techniques which are well known to those skilled in this art.

The release of the encapsulated species occurs during application by crushing the capsules under pressure exerted by the user. Mixing of the compounds takes place during spreading of the product onto the skin.

Irrespective of the embodiment of the invention and its application (cosmetic or dermatological), the subject compositions may also contain any other cosmetically or dermatologically acceptable constituent typically formulated into this type of composition, such as ionic or non-ionic thickeners, softeners, antioxidants, opacifiers, stabilizers, emollients, organic sunscreens which are active in the UV-A and/or UV-B region, photoprotective inorganic pigments and nanopigments, moisturizers, vitamins, fragrances, preservatives, fillers, sequestering agents and dyestuffs and colorants.

Naturally, one skilled in this art will take care to select this or these optional complementary compounds and/or the amounts thereof such that the advantageous properties intrinsically associated with the compositions of the invention are not, or are substantially not, adversely affected by the addition or additions envisaged.

In the compositions of this invention, each of the formulations containing either the DHA derivative or the compound capable of cleaving a carbonic ester bond may be in the form of a cream, a milk, a gel, a cream-gel, a fluid lotion, an oil-in-water emulsion or a water-in-oil emulsion, a vesicle dispersion or any other form generally employed in this art.

The DHA derivatives suited as insect repellents are described in "Unsymmetrical Carbonates as Potential Long-Lasting Insect Repellents", L. R. Garson and D. D. Garner, *Journal of Pharmaceutical Sciences*, Vol. 60, No. 7, July 1971. This article in no event suggests that these compounds are active for the coloration of the skin and constitute DHA precursors.

The present invention, thus, also features novel DHA derivatives having the following general is formula (II):

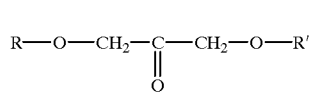

(II)

in which R and R', which may be identical or different, are each a hydrogen atom or an alkyloxycarbonyl or arylalkyloxycarbonyl radical which is optionally hydroxylated or which contains a cyclic carbonate or an oxide ether bridge, such radical having from 2 to 25 carbon atoms, linear or branched or cyclic, and saturated or unsaturated, with the provisos that (a) R and R' cannot simultaneously each be a hydrogen atom, (b) R and R' cannot simultaneously each be a 2-phenoxyethyloxycarbonyl radical, and (c) if R (or R' respectively) is hydrogen, then R' (or R respectively) is other than the following radicals:

2-ethyl-3-hydroxyhexyloxycarbonyl,
2-ethylhexyloxycarbonyl, 2-ethylpropyloxycarbonyl,
2-phenoxyethyloxycarbonyl, 3-benzyloxy-2-ethylhexyloxycarbonyl.

In a preferred embodiment of the invention, the radicals R and R' have from 2 to 18 carbon atoms.

Preferably also, R and R' are each an ethyloxycarbonyl, benzyloxycarbonyl, octyloxycarbonyl, oleyloxycarbonyl, isopropyloxycarbonyl, decyloxycarbonyl or carbonyldioxy-2,3-propyloxycarbonyl radical, and, even more preferably, the radicals R and R' are identical.

Advantageously, the derivative is selected from the group consisting of:
1,3-diethylcarbonato-2-propanone,
1,3-diisopropylcarbonato-2-propanone,
1,3-didecylcarbonato-2-propanone,
1,3-di(carbonyldioxy-2,3-propylcarbonato)-2-propanone.

The compounds of formula (II) can be prepared by reacting dihydroxyacetone with one equivalent of pyridine and one equivalent of an alkyl chloroformiate. This process constitutes another aspect of the present invention.

According to this general process, the specific compounds of formula (II) for which the radical R (respectively R') is hydrogen and the radical R' (respectively R) is a —(CO)—O—R$_1$, group, —(CO)—O—R$_1$ having the same definition as indicated above for R or R' distinct from hydrogen, are prepared from the corresponding alkyl chloroformiate of the following formula (III):

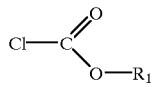
(III)

The compounds of the following formula (IV) are thus obtained:

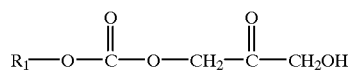
(IV)

in which —(CO)—O—R$_1$ has the same definition as R or R' in the above formula (II).

According to the same process, the specific compounds of formula (II) wherein both R' and R are simultaneously different from hydrogen are prepared by reacting a compound of the above formula (IV) with an equivalent of pyridine and an equivalent of an alkyl chloroformiate of the following formula (V):

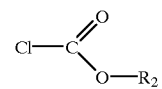
(V)

in which —(CO)—OR$_2$ has the same definition as indicated above for —(CO)—O—R$_1$.

The compounds of the following formula (VI) are thus obtained:

The present invention thus features the formulation of cosmetic/dermatological compositions as described above into preparations intended for the artificial tanning and/or browning of the skin.

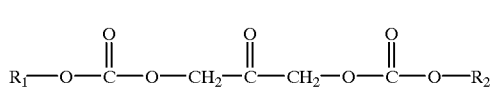
(VI)

This invention also features a regimen for the cosmetic treatment of the skin intended to artificially tan and/or brown same, comprising topically applying thereto an effective amount of a cosmetic/dermatological composition as described above.

The present invention lastly features the use of DHA derivatives as described above as DHA precursors.

In order to further illustrate the present invention and the advantages thereof, the following specific examples are given, it being understood that same are intended only as illustrative and in nowise limitative.

EXAMPLE 1

Synthesis of 1,3-diethylcarbonato-2-propanone 10 g of dimeric dihydroxyacetone were suspended in 100 cm$^3$ of dichloromethane under a nitrogen atmosphere. The mixture was cooled to 5° C. and 25 cm$^3$ of pyridine were then added. 30 cm$^3$ of ethyl chloroformate were thereafter added dropwise.

After reacting for eight hours, the insoluble fraction was filtered off and the organic phase was then washed with water. It was dried and then evaporated under reduced pressure.

The precipitate obtained was filtered through a sinter funnel. A product (11 g, 42% yield) having the following characteristics was recovered obtained:
(a) white powder
(b) m.p. (melting point): 67° C.
Elemental analysis: Theory: % C: 46.16 % H: 6.03 % O: 47.82 Found: % C: 45.99 % H: 6.03 % O: 47.94

EXAMPLE 2

Synthesis of 1,3-diisopropylcarbonato-2-propanone

The procedure of Example 1 was repeated, except that the chloroformate was isopropyl chloroformate.

A product having the following characteristics was obtained:
(b) m.p.: 40.5° C.
Elemental analysis: Theory: % C: 50.38 % H: 6.92 % O: 42.70 Found: % C: 50.61 % H: 6.93 % O: 42.55

EXAMPLE 3

Synthesis of 1,3-di(carbonyldioxy-2,3-propylcarbonato)-2-propanone

The procedure of Example 1 was repeated, except that the chloroformate was 2,3-carbonyldioxypropyl chloroformate.

A product having the following characteristics was obtained:

(b) m.p.: 105–127° C.

Elemental analysis: Theory: % C: 41.28 % H: 3.73 % O: 54.99 Found: % C: 41.13 % H: 3.79 % O: 54.96

EXAMPLE 4

Synthesis of 1,3-didecylcarbonato-2-propanone

The procedure of Example 1 was repeated, except that the chloroformate was decyl chloroformate.

A product having the following characteristics was obtained:

(b) m.p.: 71° C.

Elemental analysis: Theory: % C: 65.47 % H: 10.11 % O: 24.42 Found: % C: 65.77 % H: 10.13 % O: 24.61

EXAMPLE 5

A specific example of a composition for the artificial tanning of the skin is next described (the amounts are expressed by weight relative to the total weight of the composition):

| Phase A: | | |
|---|---|---|
| (i) | ethanol | 53.5% |
| (ii) | 1,3-diethylcarbonato-2-propanone (Example 1) | 13% |
| (iii) | hydroxypropylcellulose marketed under the trademark "Klucel M" by Aqualon (gelling agent) | 0.3% |
| Phase B: | | |
| (iv) | butylene glycol (wetting agent) | 10% |
| (v) | water | 10% |
| Phase C: | | |
| (vi) | mixture of diethylene glycol dioctanoate/ diisononanoate marketed under the trademark "Dermol 489" by Alzo (emollient) | 8% |
| (vii) | polyoxypropylene 15 stearyl ether marketed under the trademark "Arlamol E" by ICI (emollient) | 5% |
| (viii) | fragrance | 0.2% |

This composition was formulated in the following manner: phase A was first prepared by dissolving the DHA dicarbonate in the cold alcohol. The "Klucel M" was then dispersed in this mixture using a disperser, until the "Klucel M" had completely swollen.

Phase B was then prepared by mixing together the water and the butylene glycol. Phase B was then added to phase A under cold conditions with planetary stirring.

Lastly, phase C, mixed beforehand, was added to phases A and B with planetary stirring until the mixture was completely homogeneous.

When applied to the skin, the product obtained imparted to the skin a progressively tanned coloration.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological composition suited for the artificial tanning or browning of human skin, comprising an effective amount of at least one dihydroxyacetone derivative having the following formula (I):

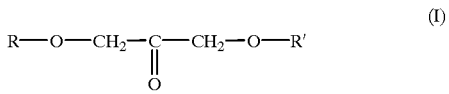

in which R and R', which may be identical or different, are each a hydrogen atom or an alkyloxycarbonyl or arylalkyloxycarbonyl radical which is optionally hydroxylated or which contains a cyclic carbonate or an oxide ether bridge, such radical having from 2 to 25 carbon atoms, being linear or branched or cyclic, and saturated or unsaturated, with the proviso that R and R' cannot simultaneously each be a hydrogen atom, in a topically cosmetically or dermatologically acceptable vehicle, diluent or carrier therefor, which is in a cosmetically/dermatologically acceptable form selected from the group consisting of a cream, milk, gel, a cream-gel, a fluid lotion, an oil-in-water emulsion, a water-in-oil emulsion, and a vesicle dispersion.

2. A topically applicable cosmetic/dermatological composition suited for the artificial tanning or browning of human skin, comprising (i) an effective amount of at least one dihydroxyacetone derivative having the following formula (I):

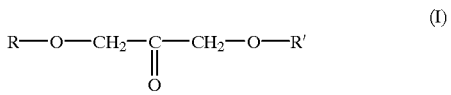

in which R and R', which may be identical or different, are each a hydrogen atom or an alkyloxycarbonyl or arylalkyloxycarbonyl radical which is optionally hydroxylated or which contains a cyclic carbonate or an oxide ether bridge, such radical having from 2 to 25 carbon atoms, being linear or branched or cyclic, and saturated or unsaturated, with the proviso that R and R' cannot simultaneously each be a hydrogen atom and (ii) at least one compound capable of cleaving at least one carbonic ester bond, in a topically cosmetically or dermatologically acceptable vehicle, diluent or carrier therefor.

3. The cosmetic/dermatological composition as defined by claim 1 or 2, wherein formula (I), the radicals R and R' have from 2 to 18 carbon atoms.

4. The cosmetic/dermatological composition as defined by claim 1 or 2, wherein formula (I), the radicals R and R' are each an ethyloxycarbonyl, benzyloxycarbonyl, octyloxycarbonyl, oleyloxycarbonyl, isopropyloxycarbonyl, decyloxycarbonyl or carbonyldioxy-2,3-propyloxycarbonyl radical.

5. The cosmetic/dermatological composition as defined by claim 1 or 2, wherein formula (I), the radicals R and R' are identical, except for the proviso that R and R' cannot simultaneously each be an hydrogen atom.

6. The cosmetic/dermatological composition as defined by claim 1 or 2, said at least one dihydroxyacetone derivative (I) selected from the group consisting of 1,3-diethylcarbonato-2-propanone, 1,3-diisopropylcarbonato-2-propanone, 1,3-didecylcarbonato-2-propanone, and 1,3-di(carbonyldioxy-2,3-propylcarbonato)-2-propanone.

7. The cosmetic/dermatological composition as defined by claim 1 or 2, said at least one dihydroxyacetone derivative comprising from 0.1% to 30% by weight thereof.

8. The cosmetic/dermatological composition as defined by claim 7, said dihydroxyacetone derivative comprising from 0.5% to 15% by weight thereof.

9. The cosmetic/dermatological composition as defined by claim 2, said at least one compound capable of cleaving at least one carbonic ester bond comprising a nucleophilic compound.

10. The cosmetic/dermatological composition as defined by claim 2, wherein said at least one compound capable of cleaving at least one carbonic ester bond is an amine or an anion.

11. The cosmetic/dermatological composition as defined by claim 10, which further comprises a compound selected from the group consisting of 3-amino-1,2-propanediol, 2-amino-2-methyl-1,3-propanediol, 2-amino-2-methylpropanol, 2-amino-2-hydroxymethyl-1,3-propanediol, glucamine, n-methylglucamine, lysine, arginine and histidine.

12. The cosmetic/dermatological composition as defined by claim 10, comprising a carboxylate anion.

13. The cosmetic/dermatological composition as defined by claim 2, said at least one compound capable of cleaving at least one carbonic ester bond comprising from 0.1% to 30% by weight thereof.

14. The cosmetic/dermatological composition as defined by claim 13, said at least one compound capable of cleaving at least one carbonic ester bond comprising from 0.5% to 15% by weight thereof.

15. The cosmetic/dermatological composition as defined by claim 2, said constituent (i) or said constituent (ii) being encapsulated.

16. A packaging confining the cosmetic/dermatological composition as defined by claim 2 in at least two physically separate compartments thereof, comprising at least one compartment confining said constituent (i) and at least one compartment confining said constituent (ii), said constituents (i) and (ii) not being in direct contact with each other.

17. The packaging as defined by claim 15, the compartments thereof being integral and constituting a single article, and permitting the expulsion and admixture of the respective constituents (i) and (ii) therefrom.

18. A dihydroxyacetone derivative having the following formula (II):

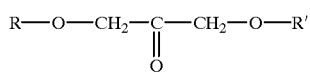
(II)

in which R and R', which may be identical or different, are each a hydrogen atom or an alkyloxycarbonyl or arylalkyloxycarbonyl radical which is optionally hydroxylated or which contains a cyclic carbonate or an oxide ether bridge, such radical having from 2 to 25 carbon atoms, linear or branched or cyclic, and saturated or unsaturated, with the provisos that (a) R and R' cannot simultaneously each be a hydrogen atom, (b) R and R' cannot simultaneously each be a 2-phenoxyethyloxycarbonyl radical, and (c) if R (or R' respectively) is hydrogen, then R' (or R respectively) is other than 2-ethyl-3-hydroxyhexyloxycarbonyl, 2-ethylhexyloxycarbonyl, 2-ethylpropyloxycarbonyl, 2-phenoxyethyloxycarbonyl, and 3-benzyloxy-2-ethylhexyloxycarbonyl.

19. The dihydroxyacetone derivative as defined by claim 18, wherein formula (II), the radicals R and R' have from 2 to 18 carbon atoms.

20. The dihydroxyacetone derivative as defined by claim 18, wherein formula (II), the radicals R and R' are independently selected from the group consisting of an ethyloxycarbonyl, benzyloxycarbonyl, octyloxycarbonyl, oleyloxycarbonyl, is isopropyloxycarbonyl, decyloxycarbonyl and carbonyldioxy-2,3-propyloxycarbonyl radical.

21. The dihydroxyacetone derivative as defined by claim 18, wherein formula (II), the radicals R and R' are identical except as specifically excluded by proviso (a) and (b).

22. The dihydroxyacetone derivative as defined by claim 18, selected from the group consisting of 1,3-diethylcarbonato-2-propanone, 1,3-diisopropylcarbonato-2-propanone, 1,3-didecylcarbonato-2-propanone, and 1,3-di(carbonyldioxy-2,3-propylcarbonato)-2-propanone.

23. A process for the preparation of the dihydroxyacetone derivative as defined by claim 18, comprising reacting dihydroxyacetone with an alkyl chloroformiate, in a pyridine containing reaction medium.

24. The process as defined by claim 23 for the preparation of a dihydroxyacetone derivative having the following formula (IV):

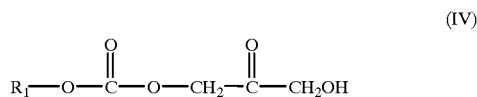
(IV)

comprising reacting dihydroxyacetone with an alkyl chloroformiate having the following formula (III):

(III)

in which —(CO)—O—$R_1$ has the same definition as R or $R^1$.

25. The process as defined by claim 23 for the preparation of a dihydroxyacetone derivative having the following formula (VI):

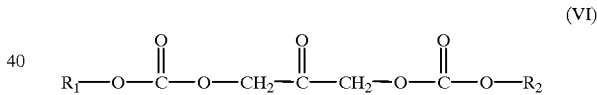
(VI)

comprising reacting dihydroxyacetone with an alkyl chloroformiate having the following formula (V):

(V)

in which —(CO)—O—$R_2$ has the same definition as —(CO)—$R_1$ which, in turn, has the same definition as R or $R^1$.

26. A regimen for artificially tanning or browning human skin, comprising topically applying thereto an effective amount of the cosmetic/dermatological composition as defined by claim 1 or 2.

27. The topically applicable cosmetic/dermatological composition of claim 1 which further comprises a cosmetically acceptable additive selected from the group consisting of a thickener, a softener, antioxidant, opacifier, stabilizer, emollient, sunscreen, photoprotective inorganic pigment or nanopigment, moisturizer, vitamin, fragrance, preservative, filler, sequestering agent, dyestuff, and a colorant.

28. The topically applicable cosmetic/dermatological composition of claim 2, which further comprises a cosmetically acceptable additive selected from the group consisting of a thickener, a softener, antioxidant, opacifier, stabilizer, emollient, sunscreen, photoprotective inorganic pigment or nanopigment, moisturizer, vitamin, fragrance, preservative, filler, sequestering agent, dyestuff, and a colorant.

29. A method for artificially tanning or browning human skin, comprising topically applying thereto an effective amount of a cosmetic/dermatological composition according to claim 3.

30. A method for artificially tanning or browning human skin, comprising topically applying thereto an effective amount of a cosmetic/dermatological composition according to claim 4.

31. A method for artificially tanning or browning human skin, comprising topically applying thereto an effective amount of a cosmetic/dermatological composition according to claim 5.

32. A method for artificially tanning or browning human skin, comprising topically applying thereto an effective amount of a cosmetic/dermatological composition according to claim 6.

33. A method for artificially tanning or browning human skin, comprising topically applying thereto an effective amount of a cosmetic/dermatological composition according to claim 27.

* * * * *